United States Patent [19]

Simmons et al.

[11] Patent Number: 4,922,027
[45] Date of Patent: * May 1, 1990

[54] PROCESS FOR THE PREPARATION OF CYCLOALIPHATIC ALDEHYDES

[75] Inventors: Dana P. Simmons, Jamestown, N.C.; Christian Chapuis, Petit-Saconnex, Switzerland

[73] Assignee: Firmenich SA, Geneva, Switzerland

[*] Notice: The portion of the term of this patent subsequent to Jan. 24, 2006 has been disclaimed.

[21] Appl. No.: 293,731

[22] Filed: Jan. 4, 1989

[30] Foreign Application Priority Data

Jan. 14, 1988 [CH] Switzerland .............................. 13388

[51] Int. Cl.$^5$ ............................................... C07C 45/45
[52] U.S. Cl. ..................................... 568/445; 568/420
[58] Field of Search ................ 568/443, 445, 447, 420

[56] References Cited
U.S. PATENT DOCUMENTS 4,800,233  1/1989  Simmons .............................. 568/447

Primary Examiner—Bruce Gray
Attorney, Agent, or Firm—Pennie & Edmonds

[57] ABSTRACT

The cycloaliphatic aldehydes of formula

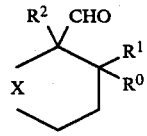 (I)

wherein $R^0$, $R^1$ and $R^2$ represent independently a hydrogen atom or a lower alkyl from $C_1$ to $C_6$ and X stands for a group of formula

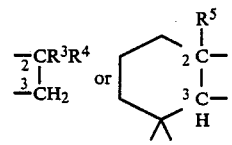

wherein $R^3$ and $R^4$ represent independenly a lower alkyl radical from $C_1$ to $C_3$ and $R^5$ represents a lower alkyl radical or hydrogen, provided that $R^1$, $R^3$ and $R^4$ do not represent simulataneously a methyl radical whenever $R^0$ and $R^2$ represent each a hydrogen atom, are prepared from enol esters of formula

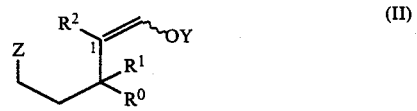 (II)

wherein the wavy line stands for a —C—O— bond of cis or trans configuration, Y represents an acyl group or P(O)(OR)$_2$, wherein R stands for a lower alkyl monovalent radical or an aryl, and Z defines a group of formula

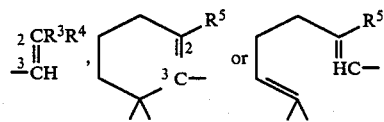

wherein $R^3$, $R^4$ and $R^5$ are defined as above, by cyclisation carried out by means of an acidic cyclisation agent.

5 Claims, No Drawings

PROCESS FOR THE PREPARATION OF CYCLOALIPHATIC ALDEHYDES

BRIEF SUMMARY OF THE INVENTION

The instant invention relates to the field of organic synthesis, more particularly it concerns a novel process for the preparation of cycloaliphatic aldehydes. The interest of these compounds resides in the fact that they are useful intermediates for the preparation of products intended for the flavor and perfume industry, as well as for the preparation of biologically active compounds, in particular from the drimane series.

European patent application No. 255,904, filed on July 25, 1987 by the applicant and published on Feb. 17, 1988, discloses a process for the preparation of 2,2,6-trimethyl-cyclohexane-carboxaldehyde, which process consists in the cyclisation by means of an acidic cyclisation agent of an enol ester of formula

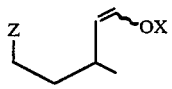

wherein the wavy line defines a —C—O— bond of cis or trans configuration, X represents an acyl group or $P(O)(OR)_2$, wherein R stands for a lower alkyl monovalent radical or an aryl and Z defines a monovalent group of formula
a. $CH=C(CH_3)_2$,
b. $CH_2—C(OH)(CH_3)_2$, or
c. $CH_2—C(CH_3)=CH_2$.

We have now established that the prinicple on which rests the said process may be applied in a perfectly analogous way to the synthesis of other cycloaliphatic aldehydes, whose structure is defind by the following general formula

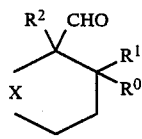 (I)

wherein each of the symbols $R^o$, $R^1$ and $R^2$ represent, when taken individually, a hydrogen atom or a lower alkyl from $C_1$ to $C_6$ and X stands for a group of formula

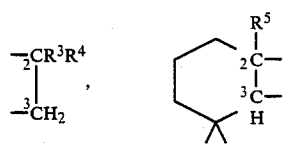

wherein $R^3$ and $R^4$ represent, when taken individually, a lower alkyl radical from $C_1$ to $C_3$ and $R^5$ stands for a lower alkyl radical or hydrogen, provided that $R^1$, $R^3$ and $R^4$ do not represent simultaneously a methyl radical whenever $R^o$ and $R^2$ represent each a hydrogen atom.

THE INVENTION

The instant invention provides a process for the preparation of aldehydes of formula (I) which process consists in the cyclisation by means of an acidic cyclisation agent of an enol ester of formula

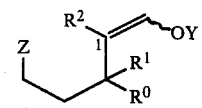 (II)

wherein the wavy line stands for a —C—O— bond of cis or trans configuration, Y represents an acyl group or $P(O)(OR)_2$, wherein R stands for a lower alkyl monovalent radical or an aryl, and Z defines a group of formula

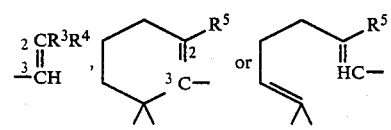

wherein $R^3$, $R^4$ and $R^5$ are defined as above.

The radical R can therefore represent an alkyl group $C_1-C_6$, for example methyl, ethyl, propyl or isopropyl or a phenyl group and Y stands for an acyl group of the type $R'CO$, $R'$ being preferably a lower alkyl radical from $C_1$ to $C_4$.

These esters, like the other dialkylphosphate esters defined by formula (II), may be prepared from aldehydes of formula

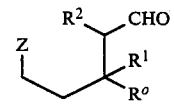 (III)

wherein symbols $R^o$, $R^1$, $R^2$ and Z have the above mentioned meaning, according to a process analogous to prior ones described in the literature [see for example: J. Am. Chem. Soc. 72, 2617 (1950)]. For example, their preparation can be effected by treating the aldehydes of formula (III) with acetic anhydride in the presence of a basic agent such as a tertiary amine, e.g. triethylamine, or in the presence of an alkali carbonate, for instance, sodium carbonate.

Acidic cyclisation agents that can be used include protic, organic or mineral acids or Lewis type acids. Among the preferred gents are sulphuric, phosphoric, polyphosphoric, methanesulfonic, acetic or trifluoroacetic acids, or yet, among the Lewis acids, tin tetrachloride, titanium tetrachloride or boron trifluoride, for example.

The temperarture at which the cyclisation reaction is carried out is not critical and can vary within a considerably large range of values. It is generally chosen as a function of the acidic agent used. Thus, good yields of end-products have been obtained at 0° C. using sulphuric acid as acidic agent. Likewise, very good yields were obtained by treating enol esters with phosphoric acid, for example 85% phosphoric acid, or polyphosphoric acid at 100° C. Temperatures above or below the cited limits can also be used.

Preferred embodiments of the process according to the invention will be described in the following specific preparaton examples. The process of the invention possesses clear advantages over the known prior art processes for the preparation of aldehydes such as those defined by formula (I), namely with regard to the simplicity of the operations required, resulting in overall economy. Furthermore, the process of the invention has the major advantage of making it possible, henceforward, to prepare optically active aldehydes since the cyclisation which characterizes the process is surprisingly accompanied by the retention of the configuration characteristic of the starting enol ester.

The invention will be illustrated in the following examples wherein the temperatures are indicated in degrees centigrade and the abbreviations have the meaning common in the art.

EXAMPLES

General Method

A concentrated solution of the starting enol ester in toluene is admixed to 85% phosphoric acid (3.5 mole equivalents) and to an identical volume of toluene. The mixture is then heated to 100° for 2 h and, after cooling to room temperature, poured in water and extracted with toluene. The combined organic extracts are then washed with an aqueous solution saturated in sodium bicarbonate and with an aqueous solution saturated in sodium chloride, then dried on anhydrous sodium sulphate and concentrated. The desired aldehydes are finally obtained by fractional distillation.

The following aldehydes were prepared according to the above described method:

1. 2,2,6,6-tetramethyl-1-cyclohexanecarbaldehyde

B.p. 45°/6.6×10$^2$ Pa; yield: 75%;
IR: 1710, 2710 cm$^{-1}$;
NMR (360 MHz): 0.94; 1.17 (2s, 12H); 9.91 (d, J=5 Hz, 1H) delta ppm;
MS: M$^+$=168(2); m/e: 153(3), 135(11), 125(18), 112(5), 109(21), 95(18), 85(100), 72(19), 69(63), 55(40), 41(32).

2. 1 alpha,2,2,6 alpha-tetramethyl-1-cyclohexanecarbaldehyde

B.p. 86°-7°/20×10$^2$ Pa; yield: 27%;
IR: 900, 1145, 1370, 1450, 1700, 3000 cm$^{-1}$;
NMR (360 MHz): 0.73(d, J=7, 3H); 0.84(s, 3H); 0.95(s, 3H); 1.12(s, 3H); 2.35(m, 1H); 9.62(s, 1H) delta ppm;
MS: M$^+$=168(5); m/e: 153(9), 135(11), 125(7), 109(24), 83(72), 69(83), 57(85), 41(100).

3. 2,6 alpha-dimethyl-2 alpha-ethyl-1 beta-cyclohexanecarbaldehyde

B.p. 89°-92°/21,3×10$^2$ Pa; yield: 42%.

4. 2,6,6-trimethyl-2-butyl-1-cyclohexanecarbaldehyde

Yield: 30%;
IR: 1710, 2710 cm$^{-1}$;
NMR (360 MHz): 0.88(t, J=13, 3H); 0.93(s, 3H); 1.17-1.18(2s, 6H); 9.89; 9.92(2d, J=5, 1H) delta ppm;
MS: M$^+$=210(1); m/e: 192(2), 177(8), 163(17), 149(5), 135(13), 125(22), 109(51), 95(42), 85(100), 69(83), 55(59), 41(44).

5. 1 alpha-formyl-2 beta,5,5,8a alpha-tetramethyl-4a beta-decahydronaphtalene

Yield: 43%; B.p. 100°-120°/1.2×10$^2$ Pa
IR: 2925, 1720, 1455, 1387, 1379, 1193, 1170, 1035, 987 cm$^{-1}$;
NMR (360 MHz): 0.78(d, J=7, 3H); 0.84(s, 3H); 0.86(s, 3H); 1.09(s, 3H); 1.90(dq, J=13.3, 1H); 2.08(m, 1H); 9,69(d, J=4, 1H) delta ppm;
NMR($^{13}$C): 15.98(q); 18.40(t); 20.66(q); 21.67(t); 21.88(q); 27.63(d); 33.17(s); 33.52(q); 35.61(t); 38.50(s); 40.32(t); 41.96(t); 54.34(d); 70.43(d); 207.65(d) delta ppm;
MS: M$^+$=222(9); m/e: 207(11), 189(13), 138(67), 123(100), 109(62), 95(68), 84(81), 69(76), 55(59), 43(96).

The latter compound was prepared by cyclisation of the corresponding enol acetate by means of SnCl$_4$ in dichloromethane.

6. 1 alpha-formyl-5,5,8a alpha-trimethyl-4a beta-decahydronaphtalene

Yield: 36%; B.p. 140°/1.2×10$^2$ Pa
IR: 2920, 2870, 2710, 1715, 1440, 1383, 1360, 1167, 950 cm$^{-1}$;
NMR (360 MHz): 0.83(s, 3H); 0.86(s, 3H); 1.01(s, 3H); 1.15-1.73(m, 11H); 1.80-2.02(m, 3H); 9.62(d, J=2, 1H) delta ppm;
NMR ($^{13}$C): 15.51(9); 18.49(t); 21,48(t); 21.60(q); 22.07(t); 26.02(t); 33.28(s); 33.44(q); 54.63(d); 63.39(d); 206.24(d) delta ppm.
MS: M$^+$=208(6); m/e: 138(22), 123(81), 109(45), 95(86), 81(92), 69(100), 55(52), 41(30).

The general method for the preparation of the starting enol esters is illustrated by the following example: 0.063M of 3,3,7-trimethyl-oct-6-ene-1-al were added under stirring to a mixture consisting of 0.06M of triethylamine, 0.126M of acetic anhydride and 1.1 g of potassium acetate pre-heated to 80°. The reactive mixture was refluxed for approximately 7 h. After cooling to room temperature, toluene and water were added and the two phases separated. 3,3,7-Trimethyl-1,6-octadienyl acetate was then obtained as a toluene solution and finally isolated by evaporation at reduced pressure.

The other enol esters used as starting products in the process of the invention were prepared in an analogous way.

The following table lists some of the products obtained, as well as the starting materials used.

TABLE

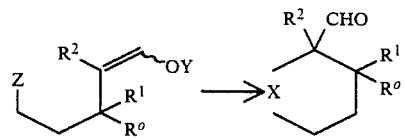

| | R$^o$ | R$^1$ | R$^2$ | X | R$^3$ | R$^4$ | R$^5$ | Z | Y |
|---|---|---|---|---|---|---|---|---|---|
| 1. | CH$_3$ | CH$_3$ | H | CR$^3$R$^4$ \| CH$_2$ | CH$_3$ | CH$_3$ | — | C(CH$_3$)$_2$ ‖ CH | CH$_3$CO |

TABLE-continued

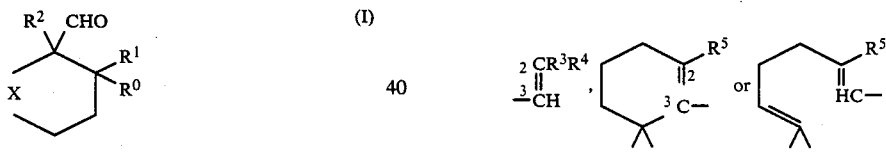

| | $R^o$ | $R^1$ | $R^2$ | X | $R^3$ | $R^4$ | $R^5$ | Z | Y |
|---|---|---|---|---|---|---|---|---|---|
| 2. | H | $CH_3$ | $CH_3$ | $\begin{array}{c}CR^3R^4\\|\\CH_2\end{array}$ | $CH_3$ | $CH_3$ | — | $\begin{array}{c}C(CH_3)_2\\||\\CH\end{array}$ | $CH_3CO$ |
| 3. | H | $CH_3$ | H | $\begin{array}{c}CR^3R^4\\|\\CH_2\end{array}$ | $C_2H_5$ | $CH_3$ | — | $\begin{array}{c}CCH_3(C_2H_5)\\||\\CH\end{array}$ | $CH_3CO$ |
| 4. | $CH_3$ | $C_4H_9$ | H | $\begin{array}{c}CR^3R^4\\|\\CH_2\end{array}$ | $CH_3$ | $CH_3$ | — | $\begin{array}{c}C(CH_3)_2\\||\\CH\end{array}$ | $CH_3CO$ |
| 5. | H | $CH_3$ | H | (cyclohexyl with $R^5$, C, C, H) | — | — | $CH_3$ | (cyclohexyl with $CH_3$, C) | $CH_3CO$ |
| 6. | H | H | H | (cyclohexyl with $R^5$, C, C, H) | — | — | H | (cyclohexyl with HC=) | $CH_3CO$ |

What we claim is:

1. A process for the preparation of cycloaliphatic aldehyde of formula $$\text{(I)}$$

(structure with $R^2$, CHO, $R^1$, $R^o$, X)

wherein $R^o$, $R^1$ and $R^2$ represent independently a hydrogen atom or a lower alkyl from $C_1$ to $C_6$ and X stands for a group of formula

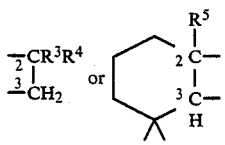

wherein $R^3$ and $R^4$ represent independently a lower alkyl radical from $C_1$ to $C_3$ and $R^5$ represents a lower alkyl radical or hydrogen, provided that $R^1$, $R^3$ and $R^4$ do not represent simultaneously a methyl radical whenever $R^o$ and $R^2$ represent each a hydrogen atom, which comprises cyclising by means of an acidic cyclisation agent an enol ester of formula $$\text{(II)}$$

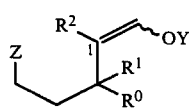

wherein the wavy line stands for a —C—O— bond of cis or transconfiguration, Y represents an acyl group or $P(O)(OR)_2$, wherein R stands for a lower alkyl monovalent radical or an aryl, and Z defines a group of formula (structures shown)

wherein $R^3$, $R^4$ and $R^5$ are defined as above.

2. A process according to claim 1, wherein the acidic cyclisation agent in a protic organic or mineral acid or a Lewis type acid.

3. A process according to claim 2, wherein the cyclisation agent is acetic acid, trifluoroacetic acid, phosphoric acid, methanesulphonic acid, boron trifluoride, titanium tetrachloride or tin tetrachloride.

4. A process a according to claim 3, wherein the cyclisation is carred out at a temperature of between about 0° and 100° C.

5. A process according to any one of the preceding claims, wherein the enol ester is an optically active enol ester of formula

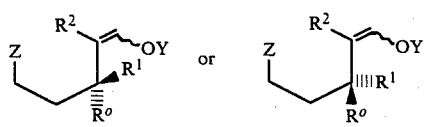

wherein Z, the wavy line and the substituents $R^o$, $R^1$ and $R^2$, as well as Y, have the meaning indicated in claim 1, and an isomerically equivalent cycloaliphatic aldehyde is obtained.

* * * * *